United States Patent [19]
Hinohara et al.

[11] Patent Number: 6,081,738
[45] Date of Patent: *Jun. 27, 2000

[54] METHOD AND APPARATUS FOR THE GUIDED BYPASS OF CORONARY OCCLUSIONS

[75] Inventors: Tomoaki Hinohara, Portola Valley; Matthew R. Selmon, Woodside; James W. Vetter, Portola Valley; Charles F. Milo, Union City, all of Calif.

[73] Assignee: LuMend, Inc., Redwood City, Calif.

[*] Notice: This patent issued on a continued prosecution application filed under 37 CFR 1.53(d), and is subject to the twenty year patent term provisions of 35 U.S.C. 154(a)(2).

[21] Appl. No.: 09/007,434
[22] Filed: Jan. 15, 1998
[51] Int. Cl.⁷ .................................................. A61B 5/05
[52] U.S. Cl. .................... 600/407; 600/464; 600/466; 606/167; 606/185
[58] Field of Search ................................ 600/427, 437, 600/462, 463, 464, 466, 467, 471, 407, 473, 476; 606/151, 152, 153, 154, 155, 156, 167, 185; 128/898; 623/1, 2

[56] References Cited

U.S. PATENT DOCUMENTS

| | | | |
|---|---|---|---|
| 3,640,270 | 2/1972 | Hoffmann | 128/2.1 E |
| 4,355,643 | 10/1982 | Laughlin et al. | 128/632 |
| 4,447,227 | 5/1984 | Kotsanis | 604/95 |
| 4,484,412 | 11/1984 | Pierpont | 604/101 |
| 4,541,433 | 9/1985 | Baudino | 128/668 |
| 4,631,052 | 12/1986 | Kensey | 604/22 |
| 4,648,402 | 3/1987 | Santos | 128/345 |
| 4,698,057 | 10/1987 | Joishy | 604/176 |
| 5,000,185 | 3/1991 | Yock | 128/662.03 |
| 5,001,556 | 3/1991 | Nakamura et al. | 358/98 |
| 5,019,040 | 5/1991 | Itaoka et al. | 604/95 |
| 5,085,221 | 2/1992 | Ingebrigtsen et al. | 128/660.1 |
| 5,099,845 | 3/1992 | Besz et al. | 128/653.1 |
| 5,099,850 | 3/1992 | Matsui et al. | 128/662.06 |
| 5,102,390 | 4/1992 | Crittenden et al. | 604/96 |
| 5,109,867 | 5/1992 | Twyford | 128/772 |
| 5,114,414 | 5/1992 | Buchbinder | 604/95 |
| 5,125,410 | 6/1992 | Misono et al. | 128/662.06 |
| 5,158,564 | 10/1992 | Schnepp-Pesch et al. | 606/159 |
| 5,181,514 | 1/1993 | Solomon et al. | 703/660.09 |
| 5,193,546 | 3/1993 | Shaknovich | 128/622.06 |
| 5,203,338 | 4/1993 | Jang | 128/662.06 |
| 5,247,938 | 9/1993 | Silverstein et al. | 128/662.03 |
| 5,256,141 | 10/1993 | Gencheff et al. | 604/53 |
| 5,279,565 | 1/1994 | Klein et al. | 604/105 |

(List continued on next page.)

FOREIGN PATENT DOCUMENTS

| | | | |
|---|---|---|---|
| 0 117 519 A1 | 9/1984 | European Pat. Off. | A61B 17/22 |
| 0 245 211 A1 | 11/1987 | European Pat. Off. | A61M 25/00 |
| 0 377 269 A1 | 7/1990 | European Pat. Off. | A61M 25/01 |

(List continued on next page.)

Primary Examiner—Brian L. Casler
Attorney, Agent, or Firm—Wilson, Sonsini, Goodrich & Rosati

[57] ABSTRACT

Described herein is a catheter method and apparatus for the guided intraluminal bypass of a coronary occlusion. A method is described employing an intraluminally operable catheter shaft including an optionally steerable working element, combined with an extraluminally operable locator including an imaging device, to selectively direct the working element to create a fluid path from the artery proximal to the occlusion into the vein and further from the vein back into the artery distal to the occlusion, to perfuse myocardium distal to the occlusion. Methods are described for creating a fluid path from the artery proximal to the occlusion into an adjacent vein and thereafter either stent grafting the fluid path to the vein, directing arterial blood distally within the vein, or stenting the fluid path and occluding the vein proximal thereto, in either case arterializing the venous system distal to the stent or stent graft. A catheter shaft is described for creating and perfusing the fluid path. Conical, guide wire and tissue-penetrating working elements are described. A scanning acoustic transducer and flexible imaging tube, and suction devices for anchoring are described for the locator. A signal-emitting working element and signal-detecting locator cooperating therewith are described.

20 Claims, 8 Drawing Sheets

U.S. PATENT DOCUMENTS

| | | | |
|---|---|---|---|
| 5,306,244 | 4/1994 | Shiber | 604/53 |
| 5,321,501 | 6/1994 | Swanson et al. | 356/345 |
| 5,325,845 | 7/1994 | Adair | 128/4 |
| 5,325,860 | 7/1994 | Seward et al. | 128/662.06 |
| 5,336,252 | 8/1994 | Cohen | 607/119 |
| 5,350,377 | 9/1994 | Winston et al. | 606/15 |
| 5,383,467 | 1/1995 | Auer et al. | |
| 5,386,828 | 2/1995 | Owens et al. | 128/653.1 |
| 5,409,453 | 4/1995 | Lundquist et al. | 604/22 |
| 5,419,767 | 5/1995 | Eggers et al. | 604/114 |
| 5,423,846 | 6/1995 | Fischell | 606/180 |
| 5,425,705 | 6/1995 | Evard et al. | 604/28 |
| 5,439,000 | 8/1995 | Gunderson et al. | 128/664 |
| 5,452,733 | 9/1995 | Sterman et al. | 128/898 |
| 5,459,570 | 10/1995 | Swanson et al. | 356/345 |
| 5,474,065 | 12/1995 | Meathrel et al. | 128/640 |
| 5,486,170 | 1/1996 | Winston et al. | 606/16 |
| 5,501,698 | 3/1996 | Roth et al. | 606/205 |
| 5,507,295 | 4/1996 | Skidmore | 128/662.06 |
| 5,507,795 | 4/1996 | Chiang et al. | 606/167 |
| 5,531,677 | 7/1996 | Lundquist et al. | 604/22 |
| 5,549,542 | 8/1996 | Kovalcheck | 600/146 |
| 5,569,276 | 10/1996 | Jang et al. | 606/159 |
| 5,571,215 | 11/1996 | Sterman et al. | 623/66 |
| 5,573,531 | 11/1996 | Gregory | 606/14 |
| 5,607,421 | 3/1997 | Jeevanandam et al. | 606/15 |
| 5,651,378 | 7/1997 | Matheny et al. | 128/989 |
| 5,676,151 | 10/1997 | Yock | 128/662.06 |
| 5,702,368 | 12/1997 | Stevens et al. | 604/171 |
| 5,704,898 | 1/1998 | Kokish | 600/141 |
| 5,709,693 | 1/1998 | Taylor | 606/145 |
| 5,743,876 | 4/1998 | Swanson | 604/96 |
| 5,799,655 | 9/1998 | Jang et al. | 128/662.06 |
| 5,807,388 | 9/1998 | Jeevanandam et al. | 606/15 |
| 5,830,222 | 11/1998 | Makower | 606/159 |
| 5,836,882 | 11/1998 | Frazin | 600/462 |
| 5,868,760 | 2/1999 | McGuckin, Jr. | 606/139 |
| 5,876,373 | 3/1999 | Giba et al. | 604/95 |
| 5,885,238 | 3/1999 | Stevens et al. | 604/4 |
| 5,968,064 | 10/1999 | Selmon et al. | 606/189 |

FOREIGN PATENT DOCUMENTS

| | | | |
|---|---|---|---|
| 1585065 | 9/1970 | France | |
| 2945237 A1 | 5/1981 | Germany | A61B 17/22 |
| 4429117 A1 | 2/1996 | Germany | A61M 29/00 |
| PCT/US96/16268 | of 0000 | WIPO | A61B 19/00 |
| PCT/US96/16483 | of 0000 | WIPO | A61B 17/00 |
| PCT/US97/01459 | of 0000 | WIPO | A61M 29/00 |
| PCT/US97/01463 | of 0000 | WIPO | A61M 19/00 |
| PCT/US97/01468 | of 0000 | WIPO | A61M 29/00 |
| WO83/03188 | 9/1983 | WIPO | A61B 1/06 |
| WO91/19528 | 12/1991 | WIPO | A61M 29/00 |
| WO92/08510 | 5/1992 | WIPO | A61M 25/00 |
| WO93/18818 | 9/1993 | WIPO | A61M 37/00 |
| WO 93/20882 | 10/1993 | WIPO | A61M 29/02 |
| WO95/19143 | 7/1995 | WIPO | A61B 17/22 |
| WO96/01590 | 1/1996 | WIPO | A61B 17/22 |
| WO 97/13463 | 4/1997 | WIPO | A61B 17/00 |
| WO 97/27897 | 8/1997 | WIPO | A61M 29/00 |
| WO98/08456 | 3/1998 | WIPO | A61B 19/00 |
| WO98/16161 | 4/1998 | WIPO | A61B 17/36 |

METHOD AND APPARATUS FOR THE GUIDED BYPASS OF CORONARY OCCLUSIONS

This application is related to U.S. patent application Ser. No. 09/008,033 and Ser. No. 09/008,198.

BACKGROUND OF THE INVENTION

1. Field of the Invention

This invention relates generally to catheters and more particularly to catheter apparatus for treating severe or total arterial occlusions. The invention relates especially to the combined use of an intraluminal transvascular catheter shaft and a minimally invasive extraluminal imaging locator to treat an occluded coronary artery.

2. Background

Atherosclerosis is a disease in which the lumen (interior passage) of an artery becomes stenosed (narrowed) or even totally occluded (blocked) by an accumulation of fibrous, fatty, or calcified tissue. Over time this tissue, known in medicine as an atheroma, hardens and occludes the artery. In the coronary arteries, which supply the heart muscle, this process leads to ischemia (deficient blood flow) of the heart muscle, angina (chest pain), and, eventually, infarction (heart attack) and death. Although drug therapies and modifications to diet and lifestyle show great promise for preventing and treating atherosclerotic vascular disease, many patients urgently require restoration of blood flow that has already been lost, especially in those having totally occluded blood vessels. Unfortunately, the demand for surgical treatment of disabling and life-threatening coronary artery disease will likely increase in the decades ahead.

It has been common surgical practice to treat severe coronary artery disease by performing a coronary bypass, in which a segment of the patient's saphenous vein (taken from the leg) is grafted onto the artery at points upstream and downstream of the stenosis. The bypass often provides dramatic relief. However, this procedure involves not only dangerous open chest surgery, but also an operation on the patient's leg to obtain the segment of saphenous vein that is used for the bypass. Additionally, there is a long, often complicated and painful, convalescence before the patient is healed. Moreover, within a few years, the underlying disease may invade the bypass graft as well. The bypass can be repeated, but at ever greater peril and expense to the patient.

Fortunately, for patients with moderate stenosis, a less traumatic operation is available. A typical mechanical device for such operations is a thin, flexible, tubular device called a catheter. Through a small, conveniently located puncture, the catheter is introduced into a major artery. Under fluoroscopic observation, the catheter is advanced and steered through the arterial system until it enters the stenosed region. At the distal (tip) end of the catheter, a balloon, cutter, or other device dilates the stenosed lumen or removes atheromatous tissue.

Cardiac catheterization procedures for treating stenoses include percutaneous transluminal coronary angioplasty (PTCA), directional coronary atherectomy (DCA), and stenting. PTCA employs a balloon to mechanically dilate the stenosis. A steerable guide wire is inserted into and through the stenosis. Next, a balloon-tipped angioplasty catheter is advanced over the guide wire to the stenosis. The balloon is inflated, separating or fracturing the atheroma. Ideally, the lumen will remain dilated for a long time. Sometimes, however, it will restenose.

In directional coronary atherectomy a catheter, containing a cutter housed in its distal end, is advanced over the guide wire into the stenosis. The housing is urged against the atheroma by the inflation of a balloon. Part of the atheroma intrudes through a window in the housing and is shaved away by the cutter.

Stenting is a procedure in which a wire or tubular framework, known as a stent, is compressed onto a balloon catheter and advanced over the guide wire to the stenosis. The balloon is inflated, expanding the stent. Ideally, the stent will hold the arterial lumen open for a prolonged period during which the lumen will remodel itself to a healthy, smooth configuration. Stents are often placed immediately following PTCA or DCA.

It must be noted, however, that a severe stenosis may be untreatable by stenting, DCA, or PTCA. The catheters used in these operations are advanced to their target over a guide wire which has already crossed the stenosis. Most guide wires, however, are too slender and soft-tipped to penetrate the calcified tissue of a total occlusion. Additionally, most guide wires have a bent steering tip which is easily trapped or diverted by the complex, hard tissues of a severe stenosis. Without a guide wire to follow, neither PTCA nor DCA nor stenting is feasible and the interventionist may have to refer the patient to bypass surgery. Additionally, degeneration makes a saphenous vein graph a risky and therefore undesirable site of intervention.

Thus, many patients would benefit from a less traumatic alternative to the bypass for restoring circulation after a coronary artery has become severely stenosed or totally occluded. In particular, many such patients would benefit from an operation for bypassing the severe stenosis or total occlusion without inflicting the gross trauma of classical bypass surgery.

It would be beneficial if a cardiologist could safely create a bypass using instruments deliverable by cardiac catheterization or through a small incision in the patient's chest. Instruments have been developed which are deliverable to the site of an occlusion by a cardiac catheter and are capable of exiting the artery through the arterial wall. U.S. Pat. No. 5,423,846 (Fischell), the disclosure of which is incorporated herein by reference in its entirety, describes a dottering auger exemplifying such a tissue-penetrating instrument. However, penetrating the arterial wall is usually what cardiac catheterization procedures strive to avoid, because perforation can easily lead to cardiac tamponade.

What is needed is a way of reliably selecting the points at which the wall of an artery can be safely penetrated by a catheter working element. What is also needed is a way of reliably guiding the working element from that point of penetration through interstitial tissues. What is also needed is a way of guiding the working element through interstitial tissue to an appropriately selected point of re-entry into the arterial system or, alternatively, an appropriately selected point of entry into the venous system.

One guidance system used in coronary catheterization is fluoroscopy, a real-time X-ray technique which is widely used to position devices within the vascular system of a patient. For visualizing a totally occluded artery, biplane fluoroscopy can be used wherein the interventionist observes two real-time x-ray images acquired from different angles. Biplane fluoroscopy, however, is unreliable, costly and slow.

Another way of imaging the coronary arteries and surrounding tissues is intravascular ultrasound, which employs an ultrasonic transducer in the distal end of a catheter. The catheter may be equipped with an ultraminiature, very high frequency scanning ultrasonic transducer designed to be introduced into the lumen of the diseased artery.

Frustratingly, however, the stenosis is often so severe that the transducer will not fit into the part that the interventionist most urgently needs to explore. Indeed, if the occlusion is too severe to be crossed by a guide wire, it may be too difficult to steer the transducer into the segment of greatest interest. Additionally, an attempt to force an imaging catheter into a severely stenosed artery may have undesirable consequences. Alternatively, the intravascular ultrasonic catheter can be placed in a vein adjacent the occluded artery. Because venous lumina are slightly broader than arterial lumina and rarely if ever stenosed, a larger transducer may be employed. Depending on its configuration, a larger transducer may acquire images over greater distances, with finer resolution, or both. However, there is not always a vein properly situated for such imaging.

While superior imaging alone is of diagnostic interest, imaging and guidance for effective intervention for severe occlusive arterial disease is what is truly desired. A reliable imaging technique is needed for discerning the relative positions of a therapeutic working element, the precise boundaries of the atheromatous tissues of an occlusion, and the structure of arteries, veins, and interstitial tissues as the working element is manipulated.

What is needed is an effective combination of a working element and a locating system for bypassing total coronary occlusions without causing cardiac tamponade. In particular, such a combination is desired which continuously displays a stable image of the atheroma, the structure of the arteries, veins, and interstitial tissues, and the working element as the interventionist maneuvers the working element. What is especially needed is such a combination which is deliverable and operable with minimal trauma to blood vessels and surrounding tissues. What is also especially needed is a method for using such a combination to create a bypass so that blood can perfuse portions of the occluded artery downstream of the occlusion.

SUMMARY OF THE INVENTION

It is an object of the present invention to treat severe or total arterial occlusions by minimally invasive means and, more particularly, to bypass the occlusion without causing uncontrolled tamponade, so that the circulation to tissues supplied by the occluded artery may be restored without physiological crisis.

It is an additional object of the present invention to safely direct an effective steerable intraluminal transvascular working element through arterial and venous walls and interstitial tissues as needed to bypass an occlusion of an artery and, in particular, to do so with the aid of a stable real-time image of the working element, occlusion, and the structures of the arteries, veins and surrounding tissues provided by an extraluminal locator device.

It is an additional object of the present invention to employ a combination of an intraluminal catheter shaft and working element and an extraluminal locator device to bypass an arterial occlusion by arterializing a vein.

It is an additional object of the present invention to take advantage of a catheter shaft including a steerable intraluminally and transvascularly operable working element to exploit the high quality image made available by a locator including an extraluminally operable imaging device. It is a related object of the present invention to position the locator proximate the occluded coronary artery through a small incision in the patient's chest.

It is an additional object of the present invention to stabilize the imaging device relative to the surface of a beating heart while the locator and catheter shaft devices are used in combination to image and operate upon the vascular system.

In accordance with the above objects and those that will be mentioned and will become apparent below, a method for bypassing an occlusion in a vascular system having a first blood vessel and a second blood vessel in accordance with the present invention comprises the steps of:

providing a catheter apparatus comprising:
an elongated flexible catheter shaft having a distal end zone and a working element disposed in the distal end zone; and
an extraluminally operable locator including an imaging device operatively disposed therein;

placing the working element in the lumen of the first blood vessel, placing the locator extraluminally proximate the first and second blood vessels, and activating the locator to observe an image of the first blood vessel, the working element therein and the second blood vessel; and while so observing, advancing the working element until the working element is observed to have established a path fluidly connecting the lumen of the first blood vessel to the lumen of the second blood vessel, whereby the locator, catheter shaft and working element cooperate to effectively bypass the occlusion.

For a preferred embodiment of the method according to the present invention, a catheter shaft includes several steering wires anchored in the distal end thereof and, optionally, a plurality of rings in the distal end zone defining paths for the steering wires. Also optionally, a plurality of slots partially circumscribe the distal end zone of the catheter shaft to provide increased flexibility. The slots provide the ability to deflect the distal end of the catheter shaft with only a gentle force supplied by the steering member. The catheter shaft also includes a working element including a tissue-penetrating wire or a nose cone. The catheter shaft is introduced via a puncture incision into the arterial system of a human patient and advanced into a coronary artery to a point proximal to an occlusion therein.

An imaging tube for this preferred embodiment includes a scanning ultrasonic imaging device and a suction cup and suction system for anchoring the imaging tube to the surface of the beating heart. The imaging tube is introduced through a small incision in the patient's chest, placed extraluminally adjacent the heart proximate the occluded artery, and anchored to the heart surface by the suction cup. Using the locator-generated image to evaluate the anatomy of the artery and of a nearby vein and of any intervening interstitial tissues, the interventionist plans a bypass path out of the artery proximal to the occlusion, across the interstitial tissues, into the vein, distally within the vein, then from the vein back to the artery distal to the occlusion. Using the locator image for guidance, the interventionist then steers the catheter shaft to an appropriate point by appying differential tension to the steering wires, activates a motor to rotate the nose cone, and advances the catheter shaft to urge the nose cone into and through the arterial wall. Continuing with guidance provided by the locator, the interventionist steers the nose cone along the planned path until the nose cone enters the artery distal to the occlusion.

Another exemplary method according to the present invention includes the steps of placing the catheter shaft in the lumen of an artery proximal to an occlusion, operating the working element to create a fluid path from the arterial lumen, through the arterial wall and interstitial tissues through the wall of an adjacent vein, and into the venous lumen, allowing arterial blood to flow into the vein. The vein distal to the fluid path is then arterialized by installing a stent graft which directs blood from the fluid path into the distal venous lumen, or by installing a stent and occluding the vein proximal to the stented fluid path. The imaging tube is stabilized and utilized as described above to provide anatomical information and guidance in planning the bypass path. Using the locator image, the interventionist guides the working element along the planned path.

In another exemplary method according to the present invention, the catheter shaft is introduced via a puncture incision into the venous system of a human patient, is advanced into a vein adjacent a coronary artery having an occlusion, and operated to create a fluid path between the vein and the artery proximal to the occlusion. The imaging tube is stabilized and utilized as described above. In this exemplary method, the fluid path can be opened, a stent placed in the fluid path, and then the vein occluded proximal to the fluid path, without delivering the occluding device or plug through the stent.

In another exemplary method according to the present invention, after the working element has created the bypass path, the catheter shaft is placed in the path, preventing the path from closing and temporarily allowing blood to flow. A catheter shaft employed in this method may include a blood perfusion lumen having proximal and distal ends in the catheter shaft. The catheter shaft is placed in the path created by the working element, allowing blood to flow through the lumen between the two blood vessels.

In an exemplary embodiment of the method according to the present invention, the working element including a tissue-penetrating wire having a sharp point. The sharp point provides the apparatus of the present invention with the ability to precisely select the point of entry of the working element into the tissue that is to be penetrated.

In another exemplary embodiment of the method according to the present invention, the working element includes a signal emitter and the locator detects the signal emitted by the emitter to discern a spatial relationship between the working element and the locator. This provides the ability to readily locate the working element.

An advantage of the present invention is that it permits the use of cardiac catheterization techniques for restoring blood flow to severely or totally occluded coronary arteries previously inaccessible to those techniques. A related advantage is that patients can enjoy relief from cardiac ischemia while avoiding the trauma of coronary bypass surgery. Another related advantage is that the native artery can be preserved and, with it, the artery's superior blood-carrying characteristics and ability to withstand repeated surgical intervention.

An additional advantage of the present invention is the ability to guide a penetrating element from an artery into an adjacent vein, or from a vein into an adjacent artery, to create a fluid path bypassing an occlusion without causing cardiac tamponade.

An additional advantage of the present invention is the ability to place a guide wire or other catheter device through such a fluid path, permitting the installation of a stent graft in the fluid path, or the placement of a stent therein and the occlusion of the vein at a point proximal to the stent, to arterialize the vein without subjecting a patient to the prolonged invasion and gross trauma of a traditional thoracotomy.

An additional advantage of the present invention is the provision of a stable, real-time image both of the arterial anatomy and of the working element that is being guided therein, allowing accurate determination of the spatial relationships of the working element, the boundaries of the occlusion, and the structures of the artery, vein, and interstitial tissues so that the working element can safely and accurately penetrate venous and arterial walls to re-route blood flow.

An additional advantage of the present invention is the effectively micro-invasive placement of the locating device in the vicinity of the occlusion, requiring only a small, minimally traumatic incision to gain access to the chest cavity.

An advantage of the present invention is that the working element and the distal end of the catheter shaft can be steered, the catheter shaft pushed, pulled or twisted, and the working element operated according to its particular design, all while the effect of these actions is immediately and continuously observable via the locator.

An additional advantage of the present invention is that the catheter shaft may be provided with a highly flexible distal end zone for precise maneuvering to exploit high resolution imaging available from the extravascularly operable locator.

An additional advantage of the present invention is the provision of a scanning ultrasound image of the catheter shaft and its anatomical environment from an imaging device which is stabilized on the surface of a beating heart. Thus, it is easier to visualize important spatial relationships while manipulating the catheter shaft and working element.

BRIEF DESCRIPTION OF THE DRAWINGS

For a further understanding of the objects and advantages of the present invention, reference should be had to the following detailed description, taken in conjunction with the accompanying drawings, in which like parts are given like reference numerals and wherein.

DETAILED DESCRIPTION OF THE INVENTION

Figure 1:
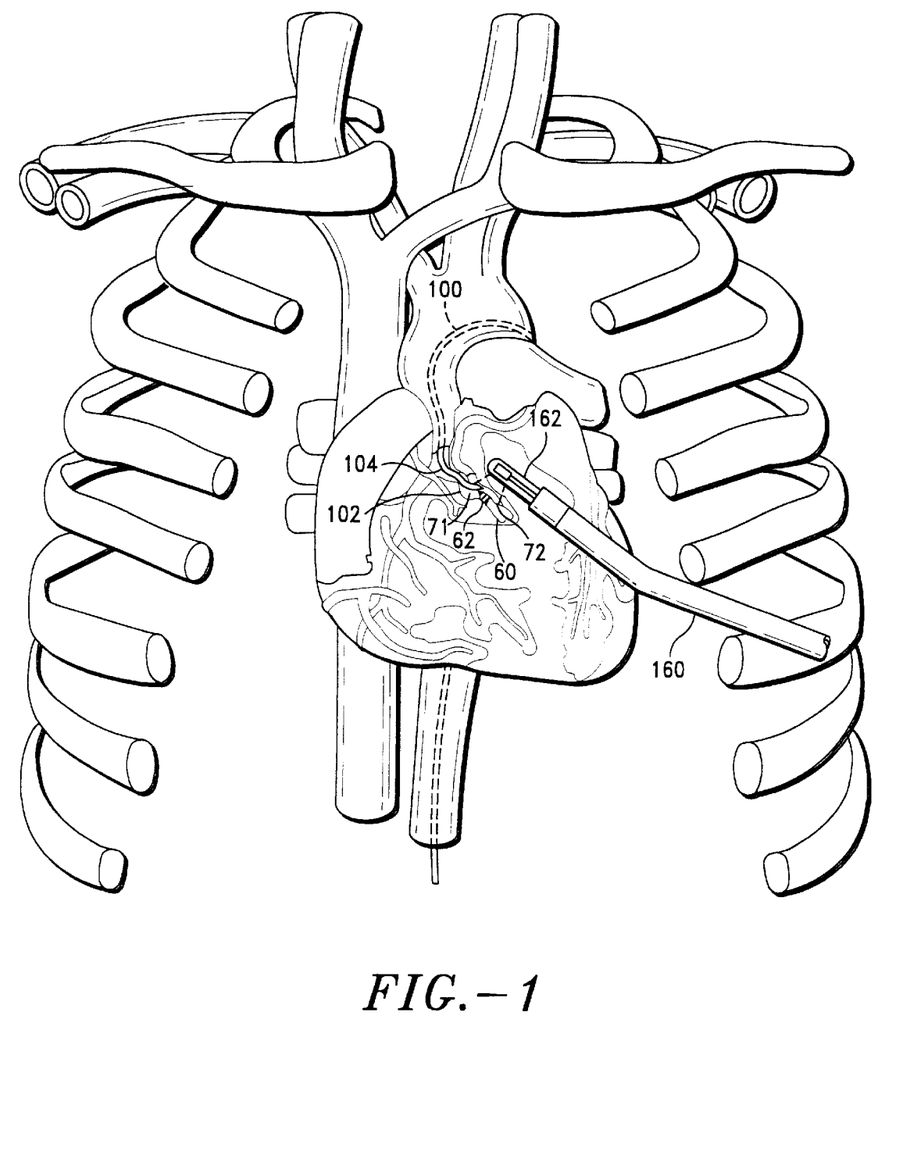
FIG. 1 illustrates an exemplary embodiment of a catheter apparatus for the method in accordance with this invention placed in a human chest cavity in a coronary artery having an occlusion.

The method of the present invention and suitable apparatus are now described particularly with reference to a coronary artery having a severe or total occlusion. As illustrated in FIG. 1, an exemplary embodiment of a catheter apparatus for the method in accordance with the present invention is shown placed proximate the occlusion 62 in a coronary artery 60. The apparatus embodies a combination of two devices which cooperate to safely bypass the occlusion 62. The first device is an intraluminally operable catheter shaft 100 including a distal end zone 104 having a working element 102 for bypassing the occlusion 62. The second device of the combination is an extraluminally operable locator 160 for locating the working element 102 with respect to the arterial lumen 71, the arterial walls 72, and the tissues and boundaries of the occlusion 62. The locator 160 includes an imaging tube 162 which is introduced through a small incision (not shown) in the patient's chest and is positioned in the chest cavity adjacent the heart and proximate the occlusion 62.

Figure 2:
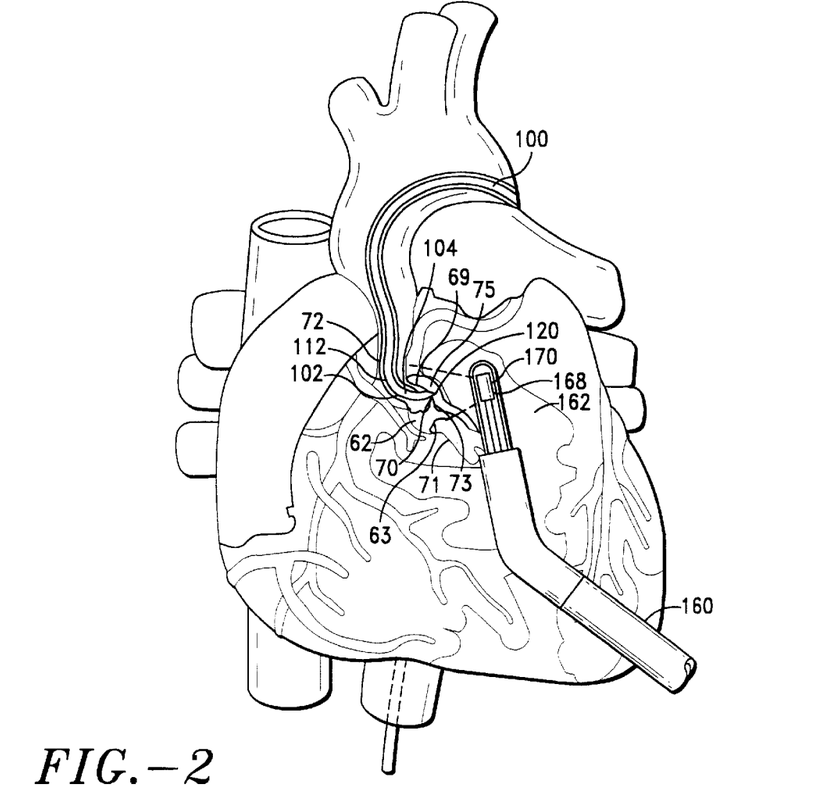
FIG. 2 is an enlarged view of the exemplary embodiment of a catheter apparatus shown in FIG. 1 placed proximate the occlusion.

Continuing with reference to FIG. 1 and now also to FIG. 2, the imaging tube 162 is introduced through an incision (not shown) which need only be large enough to slip the imaging tube 162 into the patient's chest. The imaging tube is introduced, for example, by thoracotomy, thoracoscopy or sub-xyphoid access, is passed through a puncture in the pericardium, and is advanced until it is adjacent the surface of the heart. The external imaging instruments (not shown) are then activated to display an ultrasound image.

Figure 5:
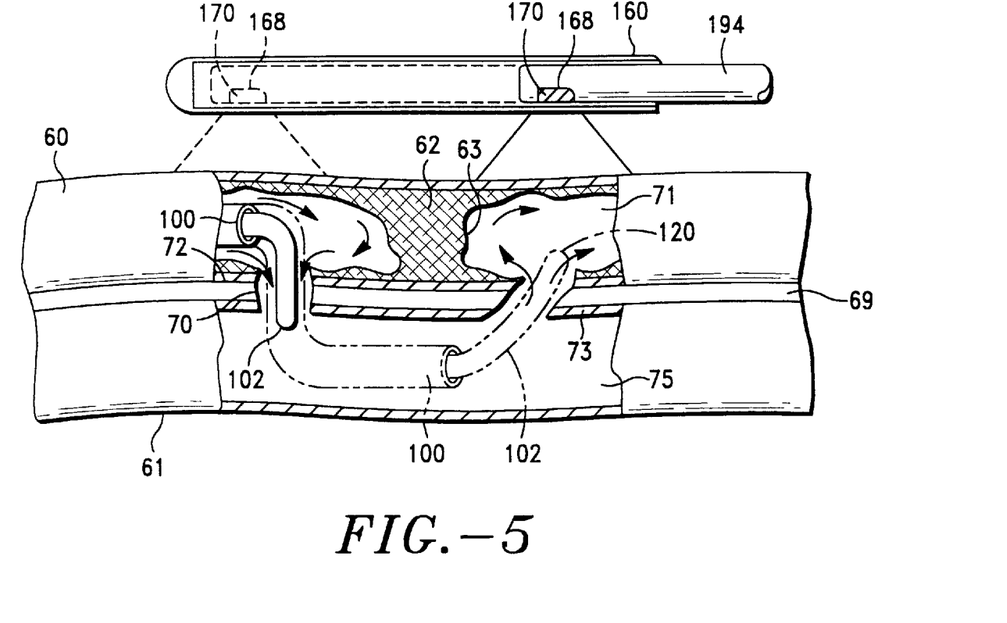
FIG. 5 is a cut-away view of an exemplary embodiment of a catheter apparatus for the method according to the present invention operating transvascularly to bypass an arterial occlusion by traversing a segment of a vein proximate an occluded artery.
Figure 6:
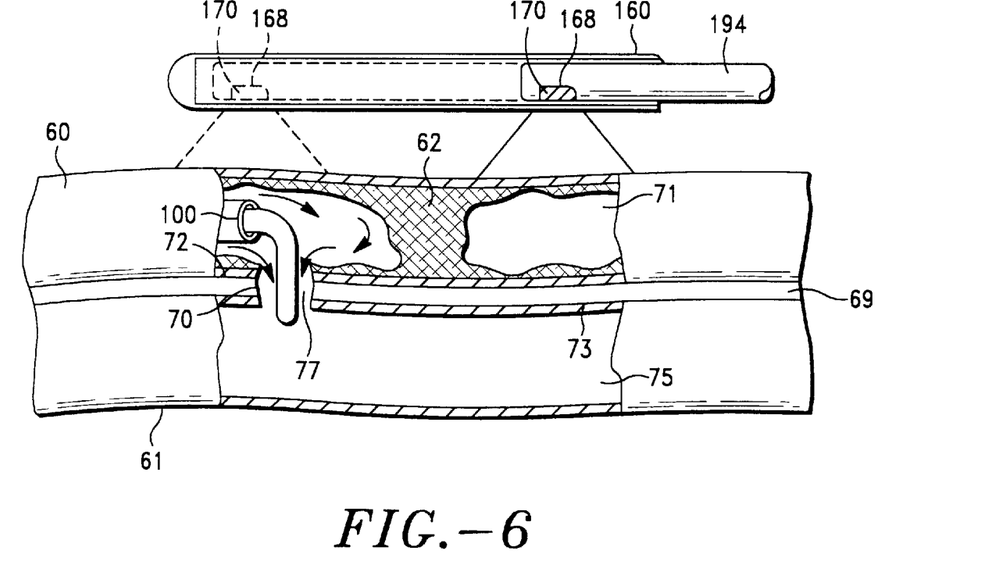
FIG. 6 is a cut-away view of an exemplary embodiment of a catheter apparatus for the method according to the present invention operating transvascularly to create a fluid path between an artery and a vein.

Referring now to FIG. 2 and also to FIGS. 5 and 6, the locator and catheter shaft are operated simultaneously to safely bypass the occlusion. Using standard catheterization techniques, the catheter shaft 100 is introduced through a puncture incision (not shown) into a major artery or vein (not shown) and is advanced and guided intraluminally into an arterial or venous branch which serves a portion of the heart. If placed in an artery, the distal end zone 104 of the catheter shaft 100 is positioned at a point proximal to (upstream of) the occlusion 62. If placed in a vein, the distal end zone 104 of the catheter shaft 100 is positioned at a point in the vein 61 adjacent a point where entry into the artery 60 is planned. The locator 160 is stabilized adjacent the heart and activated to provide an image from a vantage point close to the occluded artery 60 but outside the arterial lumen 71.

It will be appreciated that because only small punctures or incisions are needed in order for the catheter shaft and locator to reach the operation site, the patient can expect a comfortable, uncomplicated recovery. With the present method there is no need to saw through the patient's sternum or rib cage.

Figure 3:
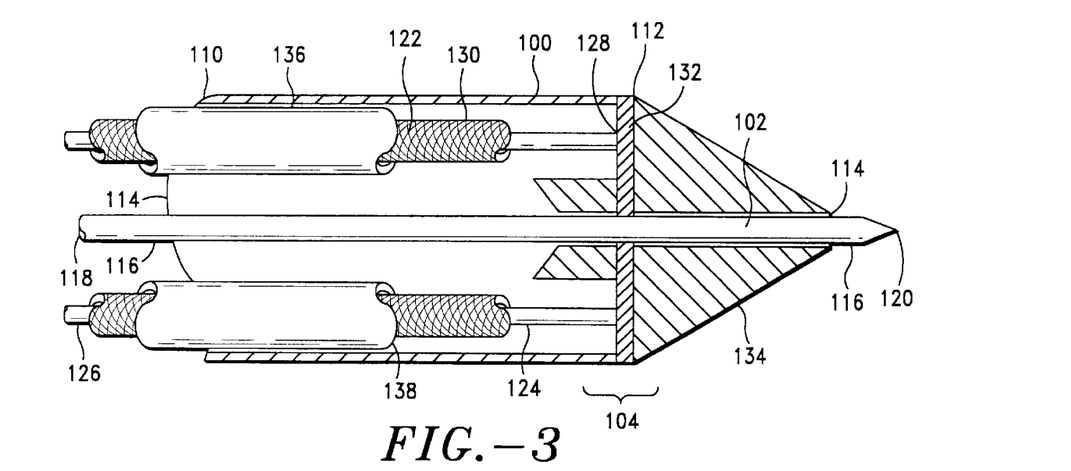
FIG. 3 is an enlarged side view of an exemplary embodiment of a catheter apparatus for the method according to the present invention showing the structure of a catheter shaft.

Referring now to FIGS. 2 and 3, the catheter shaft 100 and locator 160 are positionable with minimal trauma in the proximity of the occlusion 62 and are simultaneously operable to create a path for perfusion of the myocardium distal to the occlusion. The elongated flexible catheter shaft 100 (greatly shortened in FIG. 3) includes a steerable distal end zone 104 and a working element 102 which is carried into the proximity of the occlusion by the distal end zone 104. The proximal end zone 106 of the catheter shaft 100 is connectable to external apparatus (not shown) for manipulating the catheter shaft 100 and working element 102. The locator 160 includes an imaging tube 162 for micro-invasive placement of the imaging device 168 proximate the occluded artery 60. The imaging tube 162 includes a proximal end zone 164 connectable to external imaging instruments (not shown). The locator 160 also includes an imaging device 168 which is locatable extraluminally near the occlusion 62 and is operatively coupled to the external imaging instruments.

Referring now to FIG. 3, the catheter shaft 100 includes a proximal end 110 connectable to external apparatus (not shown), a distal end zone 104 including a distal end 112, and at least one lumen 114 therebetween. A working element 102 for penetrating tissues is disposed in the distal end zone 104. A steering member 122 is disposed in the distal end zone 104 for directing the working element 102 at and through tissues.

Continuing with respect to FIG. 3, the steering member 122 includes a plurality of steering wires 124 slidably disposed in the catheter shaft 100. The steering wires 124 have proximal ends 126 manipulable from the proximal end 110 of the catheter shaft 100 and distal ends 128 fixed in the distal end zone 104 of the catheter shaft 100. Optionally, braid-reinforced tubes 130 slidably confine the wires 124 to prevent the wires 124 from interfering with other parts of the catheter shaft 100. Also optionally, the steering wires 124 may be affixed to a retaining ring 132 disposed in the distal end zone 104 of the catheter shaft 100. Also optionally, rigid tubes 136 may be disposed about braid-reinforced tubes 130, the rigid tubes 136 having distal ends 138 some distance proximal to the distal ends 128 of the steering wires 124. Between the distal ends 138 of the rigid tubes 136 and the distal end 112 of the catheter shaft 100, the absence of the rigid tubes 136 increases the flexibility of the distal end zone 104 to facilitate steering.

As can be seen from FIG. 3, unequal tension on the steering wires 124 will deflect the distal end zone 104 of the catheter shaft 100 toward a wire 124 having greater tension. It can also be appreciated that, for example, the distal ends 128 of four steering wires 124 may be fixed in the distal end zone 104 of the catheter shaft 100 at ninety degree intervals about the longitudinal axis of the catheter shaft 100, with the result that the distal end 112 of the catheter shaft 100 can be deflected in two dimensions somewhat independently by manipulating the steering wires 124 in combination.

Continuing still with reference to FIG. 3, the working element 102 is steered by deflecting the distal end zone 104 of the catheter shaft 100. Because the working element 102 is carried in the distal end zone 104, the distal end zone 104 will impart to the working element 102 the deflection imparted to the distal end zone 104 by the steering member 122. In conjunction with the guidance provided by the locator 160 (discussed in detail below), this deflection enables an operator of the present invention to guide the working element 102 along a chosen path into and through the arterial wall 72, venous wall 62, or interstitial tissues 69.

Although the embodiment described includes the steering member, a catheter or working element without a discrete steering member and a catheter or working element without a steering function are also within the scope and spirit of the present invention. For example, the apparatus may include a guide wire and the guide wire may include a deflected distal end which functions to steer the guide wire. Likewise, the introduction of a working element into a vascular system and the operation thereof to treat an occlusion without the specific step of steering the working element during treatment is also within the scope and spirit of the method according to the present invention.

Continuing with reference to FIG. 3, an exemplary embodiment of the present invention is shown in which the working element 102 includes a tissue-penetrating wire 116 disposed in a lumen 114 of the catheter shaft 100. The tissue-penetrating wire 116 includes a proximal end 118, manipulable through the proximal end 110 of the catheter shaft 100, and a sharp distal end 120 projectable from the distal end 112 of the catheter shaft 100. Under guidance provided by the locator 160 (discussed below), pressure is applied to the proximal end of the tissue-penetrating wire 116, urging the wire 116 into and through tissues as the catheter shaft 100 and steering member 122 are manipulated to direct the wire 116.

Figure 4:
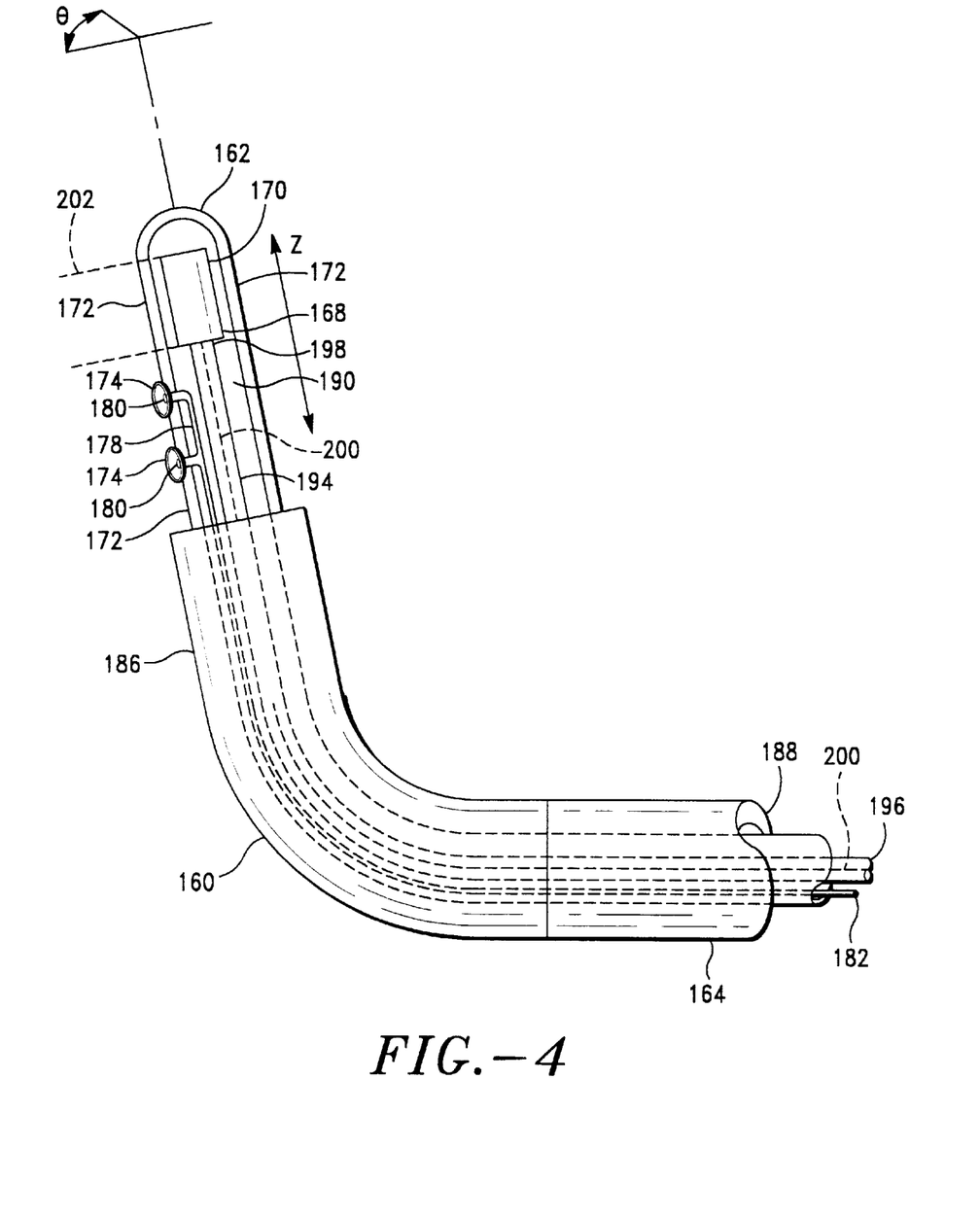
FIG. 4 is an enlarged side view of an exemplary embodiment of a catheter apparatus for the method according to the present invention showing the structure of a locator.

Referring again to FIG. 2 and now also to FIG. 4, the locator 160 includes an imaging device 168 (in this embodiment, an acoustic transducer 170), an imaging tube 162 for placing the imaging device 168 extraluminally proximate the occlusion 62, and one or more external imaging instruments (not shown) operatively coupled to the imaging device 168 for discerning the spatial interrelationships of the working element 102, occlusion 62, arterial lumen 71, arterial wall 72, venous wall 73, venous lumen 75, and interstitial tissues 69. Optionally, the imaging tube 162 has an exterior surface 172 which forms one or more suction cups 174 for stabilizing the imaging tube 162 on tissues near the artery 60 having the occlusion 62. Also optionally, the imaging tube 162 has a suction cup activator 176 for selectively activating the suction cup 174. As illustrated in FIG. 3, the activator 176 includes a lumen 178 having a distal end 180 communicating with a suction cup 174 and a proximal end 182 communicating with a pressure-modulating device (not shown). The activator 176 may, however, encompass an aspirator, a mechanical means of activating the suction cup 174, or any other convenient way of establishing and interrupting a vacuum to temporarily stabilize a surface of the imaging tube 162 upon a surface proximate the artery 60 and occlusion 62. Generally, the suction cup may take the form of any other suction-coupling area or feature, defined by a surface 172 of the imaging tube 162, which affords adhesion to a surface.

Continuing with reference to FIG. 4, it will be appreciated that the imaging tube 162 can be made flexible enough to enable the distal end zone 186 of the imaging tube 162 to be secured adjacent a beating heart while the proximal end zone 164 of the imaging tube 162 remains connected to external instruments (not shown) for support and control. The flexibility of the imaging tube 162 contributes to its microinvasive quality by reducing the trauma inflicted upon tissues and by permitting the tube 162 to conform to the natural contours of bodily surfaces. As alternative ways of reducing trauma and increasing the ease of use, the imaging tube 162 may be given a shape well suited to the route of entry into the chest, or may be stabilized or flexibly supported by external apparatus at its proximal end 188.

Continuing still with reference to FIG. 4, the imaging tube 162 includes a proximal end 188, a lumen 190 originating in the proximal end 188, and a motor assembly (not shown) proximate the proximal end 188. A transducer control shaft 194, rotatably and translatably disposed in the lumen 190, includes a proximal end 196 coupled to the motor assembly 192, a distal end 198 coupled to the transducer 170, and a signal conducting path 200 operatively coupling the transducer 170 to the external imaging instruments (not shown). The transducer control shaft 194 is flexible enough to bend with the imaging tube 162. In this embodiment, the external imaging instruments (not shown) include an acoustic signal generator-processor (not shown) and video display device controlled by a suitably programmed general purpose computer.

Continuing still with reference to FIG. 4, the locator 160 in this exemplary embodiment provides a scanning ultrasound image of the environment of the occlusion 62. The imaging tube 162 is stabilized on the heart adjacent the artery 60 containing the occlusion 62. The motor assembly (not shown) drives the transducer control shaft 194 within the lumen 190 of the imaging tube 162 in a scanning pattern appropriate for producing an image. For example, the motor assembly (not shown) may drive the transducer control shaft 194 in a repeating reciprocating pattern while at the same time rotating the shaft. In this way, the transducer 170, which is coupled to the transducer control shaft 194, describes a two-dimensional scanning pattern which may be registered by appropriate measuring devices as combinations of a rotational angle θ and a longitudinal position Z within the imaging tube 162.

Continuing still with reference to FIG. 4, as the transducer 170 describes the scanning pattern, the acoustic signal generator-processor (not shown) causes the transducer 170 to emit acoustic energy. A signal conducting path 200 carries an electric signal from the external instruments (not shown) (which include, in this illustration, a signal generator-processor, also not shown) to the transducer 170, which may include a piezoelectric crystal or other device for producing acoustic energy. This acoustic energy is of the type referred to as ultrasonic or ultrasound, although these terms may encompass a variety of acoustical signals embodying a variety of frequencies. The energy passes through the surface 172 of the imaging tube 162 and into the occluded artery 60 and surrounding tissues. The transducer 170 and acoustic signal are configured such that the energy is emitted in a narrowly focused beam 202 in a known direction (at a known value of the angle θ from a known position (at a known value of Z) with respect to the imaging tube 162. The transducer 107 also functions as a similarly directional acoustic signal detector, converting acoustic energy reflected by features in the environment of the imaging tube 162 to a signal which is conducted back to the signal generator-processor and measured accordingly. As are the emitted signals, the detected signals are associated with values of θ and Z.

Continuing still with reference to FIG. 4, a third dimension, which shall be referred to as depth or as radius from the transducer 170 and given the letter r, is computable as a function of the time elapsed between the emission of a given signal by the transducer 170 and the detection of the echo of that signal. The value detected at any given time is a function of the intensity of the echo. With appropriate signal processing, this intensity can be reported via suitable video equipment as a two or three dimensional image of the environment of the imaging tube 162. General purpose computers are programmable to accomplish this function. U.S. Pat. No. 4,794,931, the disclosure of which is incorporated herein by reference in its entirety, describes a computer and instrument system implementing such a function.

Alternatively, a rotating or translating scanning transducer may be supplanted by an array of directional transducers (not shown), a phased array of transducers (not shown) or other appropriately energized and interrogated set of transducers operatively connected to the external signal generator-processor for displaying the desired image.

Referring to FIGS. 2, 3, and 4, the locator 160 provides an image of nearby anatomical features so that the position of the locator 160 with respect to the artery 60, occlusion 62, vein 61 and interstitial tissues 69 is ascertained. The locator 160 is manipulated until its position is ideal for imaging the vessels and tissues to be penetrated. The locator 160 is then stabilized. Optionally, the imaging tube 162 has an exterior surface 172 which including one or more suction cups 174 for stabilizing the imaging tube 162 on tissues near the occluded artery 60. With the locator 160 positioned and functioning, the positions of the distal end 112 of the catheter shaft 100 and the distal end 120 of the working element 102 are ascertained. The contours of the occlusion 62, the artery 60, the adjacent vein 61, and interstitial tissues 69, as revealed by the locator 160, are also evaluated.

Referring back to FIGS. 3 and 4 and now also to FIG. 5, it is seen that the catheter shaft 100 and locator 160 are placed proximate the occlusion 62. The catheter shaft 100 and steering member 122 are manipulated to direct the working element 102 and the catheter shaft 100 at a point of penetration 70 through the arterial wall 72 for exit from the artery 60. The point of penetration 70 will have been identified in the image provided by the locator 160. The image provided by the locator 160 is also studied to determine an appropriate path around the occlusion 62. The working element 102 is then steered and advanced along that planned path under continuous observation via the locator 160. While control of the working element 102 and catheter shaft 100 is maintained via the steering member, the working element 102 and catheter shaft 100 are urged and steered though the arterial wall 72, through the interstitial tissues 69, through the wall 73 of the adjacent vein 61 and then distally within the venous lumen 75.

Continuing with reference to FIGS. 3 and 5, as the working element 102 and catheter shaft 100 are advanced, their positions with respect to these anatomical features and with respect to the occlusion 62 are carefully noted from the image provided by the locator 160. The steering member 122 is manipulated to direct the working element 102 away from any contact perceived as likely to cause cardiac tamponade. When the distal end 120 of the working element 102 reaches a point in the vein proximate the distal boundary 63 of the occlusion 62, as observed in the locator image, the steering member 122 is used to direct the working element 102 and catheter shaft 100 through the venous wall 73, across the interstitial tissues 69, and back through the arterial wall 72 into the arterial lumen 71 distal to the occlusion 62. A path has now been created bypassing the occlusion 62. Blood can now flow out of the artery 60 proximal to the occlusion 62, through the vein 61, and back into the artery 60 distal to the occlusion 62.

Referring now to FIG. 6, an exemplary method is according to the present invention is described in which the catheter shaft 100 is introduced into the arterial system and is advanced to a position in the lumen 71 of a coronary artery 60 proximal to an occlusion 62. The working element 102 is directed through the arterial wall 72 and interstitial tissues 69, through the wall 73 of an adjacent vein 61, and into the venous lumen 75 to create a fluid path 77 from the occluded artery 60 to the vein 61. Having created the fluid path 77, the interventionist is also able to place the catheter shaft 100 or a guide wire (not shown) or other catheter-borne device from the artery 60 through the path 77 into the vein 61, rendering further procedures, such as, for example, stenting or stent grafting, feasible.

Figure 7:
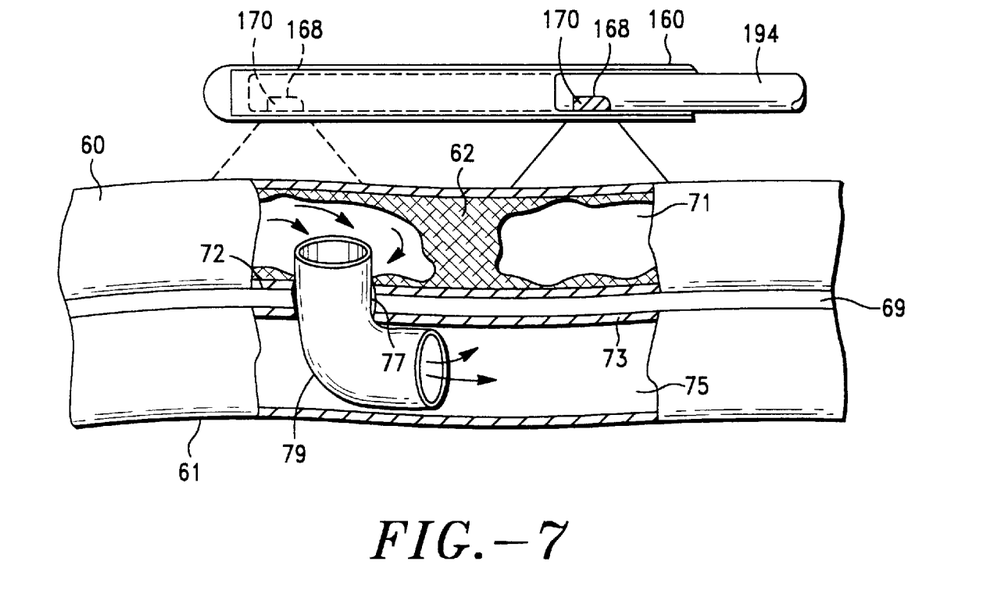
FIG. 7 is a cut-away view of an arterio-venous stent graft placed to maintain a fluid path between an artery and a vein in a step of an exemplary method according to the present invention.

FIG. 7 illustrates a stent graft 79 placed in the artery 60 and vein 61. The stent graft 79 maintains the fluid path 77 and directs the flow of blood in the distal direction within the venous lumen 75, effectively arterializing the vein 61 distal to the stent graft 77. Apparatus and methods for stent grafting are described in U.S. Pat. No. 5,549,663 (Cottone, Jr., 1996) and U.S. Pat. No. 5,122,154 (Rhodes, 1992), the entire disclosures of which are incorporated herein by reference.

Figure 8:
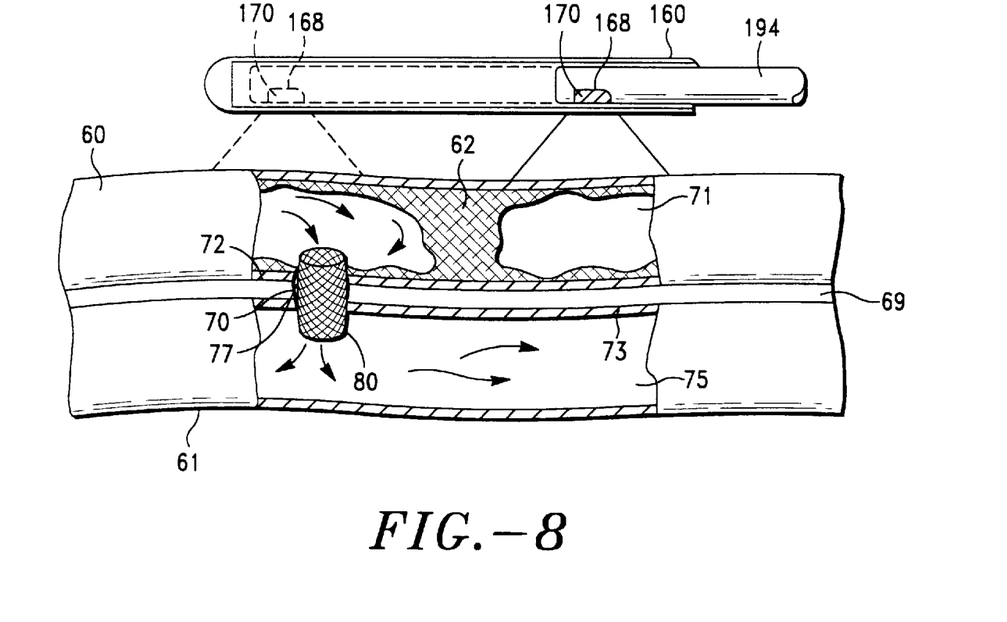
FIG. 8 is a cut-away view of an arterio-venous stent placed to maintain a fluid path between an artery and a vein in a step of an exemplary method according to the present invention.

FIG. 8 illustrates a stent 80 placed in the artery 60 and vein 61. The stent 80 maintains the fluid path 77, allowing arterial blood into the vein 61. Apparatus and methods for stenting are described in U.S. Pat. No. 4,739,762 (Palmaz, 1988) and U.S. Pat. No. 4,580,568 (Gianturco, 1986), the entire disclosures of which are incorporated herein by reference.

Figure 9:
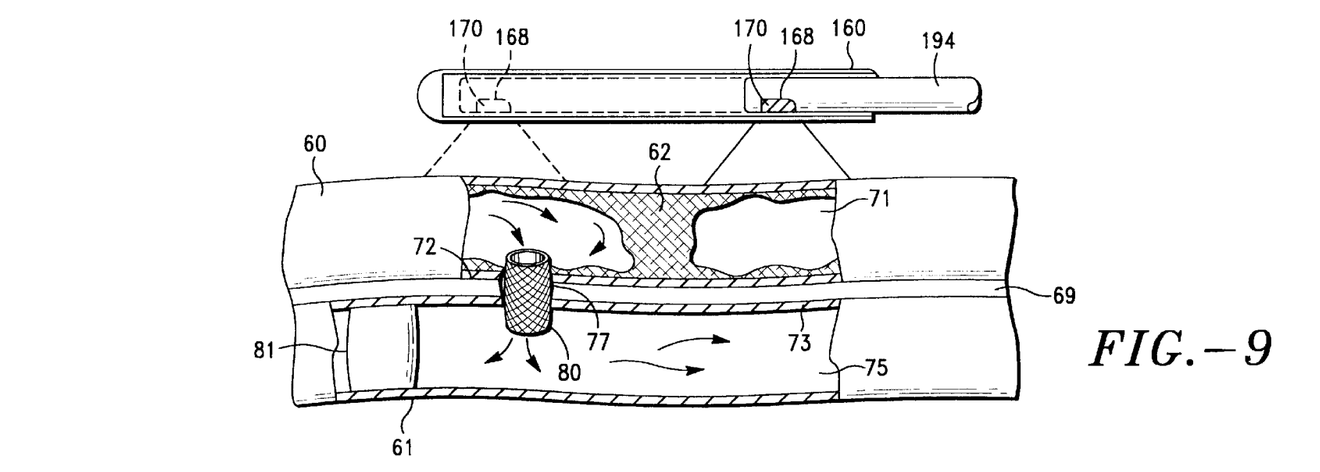
FIG. 9 is a cut-away view of venous plug placed to occlude a vein at a point proximal to a stented arterio-venous fluid path in a step of an exemplary method according to the present invention.

FIG. 9 illustrates a collagen plug 81 placed in the vein 61 proximal to the fluid path 77 and stent 80. The plug 81 occludes the vein 61, directing the flow of arterial blood from the fluid path 77 distally within the vein 61 and effectively arterializing the vein 61 distal to the fluid path 77. Apparatus and methods for occluding a vessel with such a plug are described in U.S. Pat. No. 5,540,657 (Kurjan et al., 1996), U.S. Pat. No. 5,643,464 (Rhee et al., 1997) and U.S. Pat. No. 5,658,593 (Orly et al., 1997), the entire disclosures of which are incorporated herein by reference.

It will be appreciated that, where it is appropriate to occlude the vein 61, other methods of occlusion, such as ligation, may be employed. It will also be appreciated that a catheterization procedure for occluding the vein 61 can be performed via the fluid path 77 or, alternatively, via a catheter introduced from a point of access to the venous system proximal to the fluid path 77. The latter approach may be preferable if for any reason it is inconvenient or difficult to reach proximally into the venous lumen 75 from the fluid path 77.

It will also be appreciated that the steps described above for creating the fluid path 77 may alternatively be performed from the vein 61 instead of the artery 60. For example, although FIG. 9 shows the catheter shaft 100 and working element 102 being introduced via the arterial lumen 71, the catheter shaft 100 and working element 102 can alternatively be introduced via the venous lumen 75. The fluid path 77 can first be created, then a stent 80 installed, and finally a plug 81 placed in the venous lumen 75. In this manner, the occlusion of the vein 61 by the plug 81 is effected after the stent 80 has been installed and is performed without the need to deliver the plug 80 through the stented fluid path 77.

Referring again to FIG. 2, it is seen that the catheter shaft 100 and the locator 160 of the present invention cooperate to enable the operator to guide the working element 102 into and through the arterial wall 72, venous wall 73, and interstitial tissues 69 while knowing and maintaining control of the anatomical location and orientation of the catheter shaft. In the procedures described above, the image provided by the locator 160 is observed for guidance while manipulating the catheter shaft 100, steering member 122 and working element 102. It is also within the scope of the present invention to employ, for example, a guide wire in place of a steerable working element or steerable catheter shaft.

Thus, a bypass (fluid path) can be created while avoiding uncontrolled hemorrhage or unintended trauma. After the bypass has been created, the suction cups 174 may be released, the apparatus withdrawn from the patient, and the incisions closed. Importantly, the micro-invasive locator 160 provides the necessary spatial information for guidance of the working element 102 while completely avoiding the gross trauma that would be inflicted by traditional bypass operations. Optionally, a lumen of the catheter shaft 100, such as the lumen 114, may penetrate the catheter shaft 100 at one or more points, some more proximal than others, to establish a blood perfusion path through the catheter shaft 100 while the catheter shaft 100 is placed in the bypass. Also optionally, the lumen so employed may be the same lumen 114 occupied by the working element 102. The working element 102 and lumen 114 may, for example, be configured such that advancement, withdrawal, rotation, or other manipulation of the working element 102 opens or closes the lumen 114 to the flow of blood or other fluid between two or more places where the lumen 114 communicates with the environment of the catheter shaft 100.

Referring again to FIG. 3, an exemplary embodiment of the present invention is shown including the above-described locator 160, catheter shaft 100, lumen 114, steering member 122, and tissue-penetrating wire 116. A metal nose cone 134 is included in the distal end 112 of the catheter shaft 100 and defines a distal orifice through which the tissue-penetrating wire 116 can project from the lumen 114. As the tissue-penetrating wire 116 is urged through tissues, the catheter shaft 100 can be steered via the steering member 122 and urged into the tissues along the path made by the wire 116. As the catheter shaft 100 follows the wire 116 through the tissues, the nose cone 134 reduces the resistance encountered by the catheter shaft 100. Progress is observed via the locator 160 (discussed below).

Figure 10:
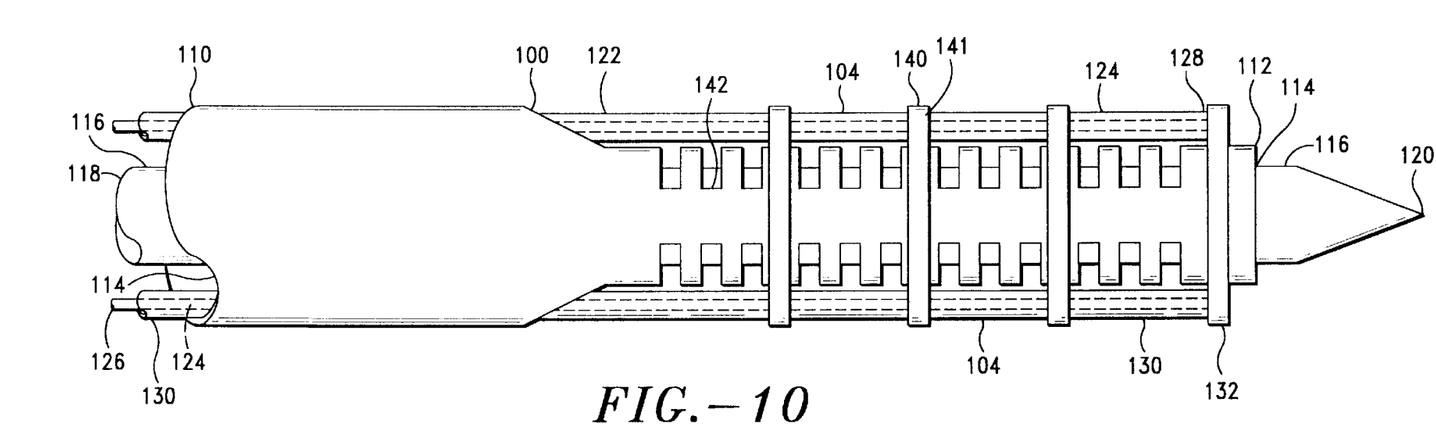
FIG. 10 is a side view of an exemplary embodiment of a catheter apparatus for the method according to the present invention showing the structure of a catheter shaft including rings and slots in the distal end zone of the catheter shaft.

Referring now to FIG. 10, an exemplary embodiment of the present invention is shown including the above-described locator 160, catheter shaft 100, lumen 114, steering member 122, and tissue-penetrating wire 116 (other work elements may be used, as will be described below). The distal end zone 104 of the catheter shaft 100 also includes a plurality of rings 140. The rings 140 define paths 141 for the steering wires 124 (described above) of the steering member 122. One or more of the rings 140 may serve to anchor the distal ends 128 of the steering wires 124. The distal end zone 104 of the catheter shaft 100 also includes a plurality of slots 142 inscribed therein for increasing the steerability of the distal end zone 104.

Continuing with reference to FIG. 10, unequal tension on the steering wires 124 will deflect the distal end zone 104 and the working element 102 toward a wire having greater tension. The slots 142 in the distal end zone 104 of the catheter shaft 100 reduce the force required to compress one side of the distal end zone 104 and extend the opposite side. A steering wire can thus more easily deflect the distal end zone 104. Because the slots 142 only partially circumscribe the distal end zone 104 of the catheter shaft 100, they do not appreciably reduce its axial stiffness. As a result, the distal end 112 of the catheter shaft may still be pushed firmly against a tissue surface at a point where the working element 102 is intended to enter.

Figure 11:
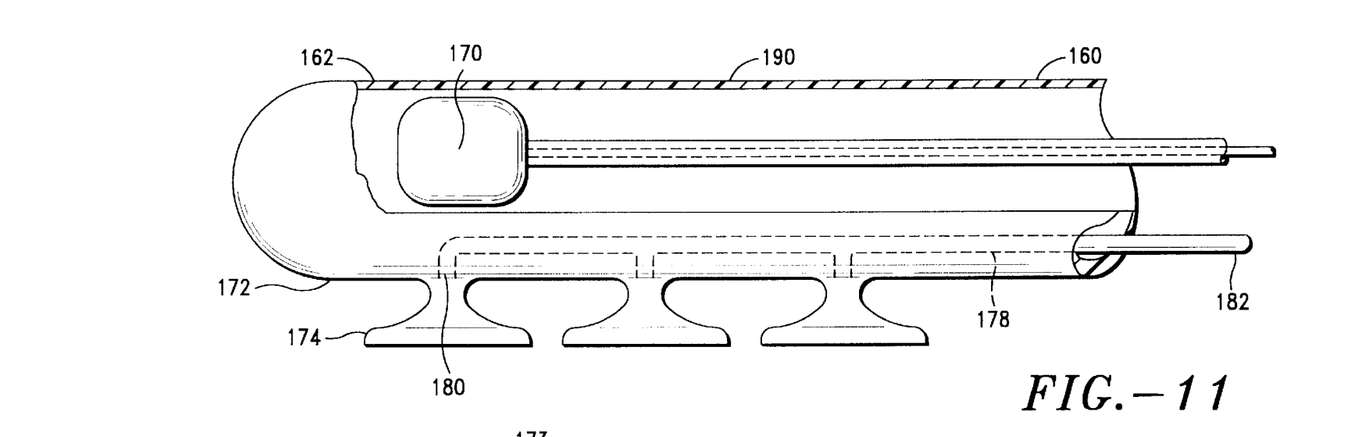
FIG. 11 is a side view of an exemplary embodiment of a catheter apparatus for the method according to the present invention showing the structure of a locator including a plurality of suction cups.
Figure 12:
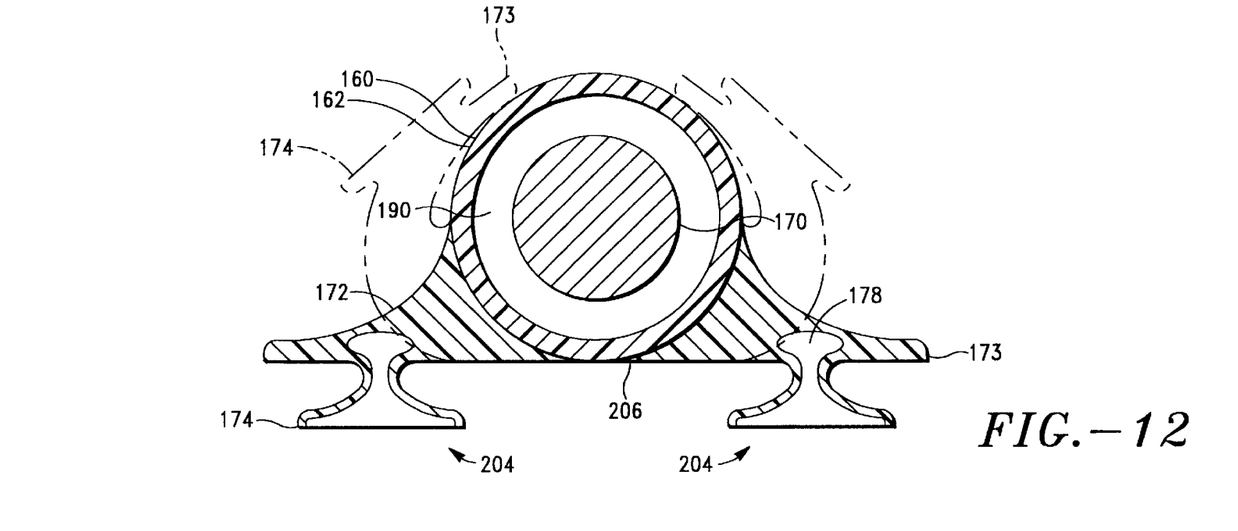
FIG. 12 is a sectional view of an exemplary embodiment of a catheter apparatus for the method according to the present invention showing the structure of a locator including a plurality of suction cups.

Referring back to FIG. 2 and now particularly to FIGS. 11 and 12, an exemplary embodiment of the present invention is shown in which the imaging tube 162 of the locator 160 includes an exterior surface 172 defining a plurality of suction cups 174. The suction cups 174 are arrayed in two roughly parallel rows 204. Between the rows 204 is a region of the surface defining an imaging window 206. In the exemplary embodiment illustrated in FIG. 12, the imaging window 206 includes an acoustically transparent portion of the imaging tube 162 adjacent the lumen 190. As can be seen in FIG. 12, the transducer 170 has a view through the window 206 unobstructed by the suction cups 174. The imaging tube 162 optionally includes a suction cup activating lumen 178 having a distal end zone 180 communicating with the suction cups 174 and a proximal end 182 coupled with a pressure modulating device (not shown). The lumen 178 and pressure modulating device permit rapid, minimally traumatic temporary stabilization of the imaging tube 160 on the heart surface.

Figure 13:
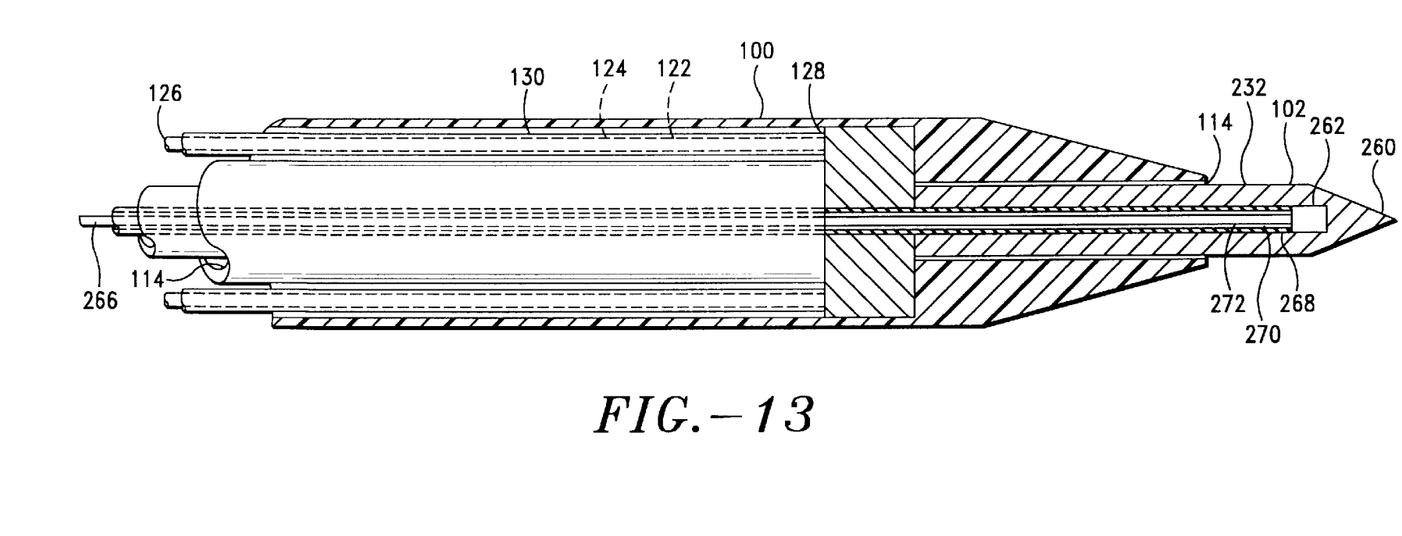
FIG. 13 is a side view of an exemplary embodiment of a catheter apparatus for the method according to the present invention showing the structure of a catheter shaft including a signal-emitting working element.

Referring back to FIG. 2 and now also to FIG. 13, an exemplary embodiment of the present invention is shown including the above-described locator 160, catheter shaft 100, lumen 114 and steering member 122. In this embodiment, the working element includes a tissue-penetrating working element 102 having a distal end 260. A signal emitter 262 is disposed in the distal end 260. A signal generator (not shown) is operatively coupled to the signal emitter 262. In this embodiment, the signal generator is external to the body and is coupled to the emitter through an electrically conductive path 266 originating in the proximal end zone 106 of the catheter shaft 100 and terminating at the emitter 262. As illustrated, the electrically conductive path includes an outer conductor 268 disposed in the catheter shaft 100, a tubular dielectric layer 270 therein, and an inner conductor 272 disposed within the dielectric layer. However, any other energy-delivering or converting means can be employed to energize the emitter 262. When the locator 160 and emitter 262 are activated within the body, the locator 160 selectively detects the signal emitted by the emitter 262 in order to discern a spatial relationship between the working element 102 and the locator 160.

Alternatively, the signal emitter 262 may be disposed in a working element which is essentially a guide wire, optionally steerable. Likewise, the catheter shaft may be of a simpler design than the one shown in FIG. 13; in particular, a catheter shaft without a steering member, and a signal-emitting guide wire distal end not surrounded by a separate catheter shaft, are both within the scope of the present invention.

While the foregoing detailed description has described several embodiments of the invention, it is to be understood that the above description is illustrative only and not limiting of the disclosed invention. Particularly, the imaging device need not be an acoustic transducer and need not accomplish its imaging by scanning or mechanical movement in any particular manner. The imaging device may be operatively coupled to external instruments by any appropriate mechanical, electromagnetic, optical, wave guide or other path. The image that is displayed may be computed by any of a variety of algorithms for extracting one-, two-, or three-dimensional information from energy reflected, scattered or absorbed within tissues. The imaging tube may be stabilized proximate the occlusion 62 by any appropriate mechanical, pneumatic, hydraulic or other means. Additionally, the locator 160 need not approach the heart in the particular manner described; alternative routes may be taken.

It will also be noted that a variety of paths, originating in one blood vessel and terminating in that vessel or another, may be followed by the working element and catheter shaft and that, depending on the configuration and support of the working element, either the catheter shaft or the working element or both may be placed in the path created by the working element. Also, either the working element or the catheter shaft may be left in the path so created to serve as a conduit or for some other purpose. The catheter shaft may include a lumen to facilitate blood flow in the bypass. The catheter shaft or work element may include a balloon for stabilization, for interruption of flow, or for other purposes.

Likewise, the steering member may include more or fewer than the two wires illustrated in the drawing figures or may be omitted for any step not necessitating steering. The working element 102 may include any mechanical, optical, thermal, chemical, or other device for penetrating tissues, treating an occlusion, or delivering a medicament. The catheter shaft 100 and working element 102 may be configured such that only the working element 102 traverses certain tissues or, alternatively, the catheter shaft 100 itself may follow along with the working element 102. It will be appreciated that the embodiments discussed above and the virtually infinite embodiments that are not mentioned could easily be within the scope and spirit of the present invention. Thus, the invention is to be limited only by the claims as set forth below.

What is claimed is:

1. A method for bypassing an occlusion in a vascular system, comprising the steps of:
   providing a catheter apparatus comprising,
      an elongated flexible catheter shaft having a distal end zone and a working element disposed in the distal end, and wherein the catheter shaft is formed with a lumen that includes a tissue-penetrating wire at least partially disposed in the lumen of the catheter shaft; and
      a locator comprising an imaging tube and an imaging device operatively disposed therein;
   placing the working element in the lumen of the first blood vessel, and activating the locator to observe an image of a first blood vessel, the working element therein and a second blood vessel;
   manipulating the working element using a steering member comprising a plurality of steering wires slidably disposed in the catheter shaft and coupled to a retaining ring disposed in the distal end zone, wherein braid-reinforced tubes confine each of the plurality of steering wires; and
   advancing the working element to establish a path fluidly connecting the lumen of the first blood vessel to the lumen of the second blood vessel.

2. A method as set forth in claim 1, wherein the first blood vessel is an artery.

3. A method as set forth in claim 2, further comprising the step of introducing the catheter shaft into the arterial system and operating the steering member to steer the working element.

4. A method as set forth in claim 1, wherein the first blood vessel is a vein.

5. A method as set forth in claim 1, further providing the working element and the catheter shaft as a guide wire.

6. A method as set forth in claim 5, further providing the guide wire with a steering wire to steer the guide wire.

7. A method as set forth in claim 1, wherein a bodily surface is proximate the first and second blood vessels and the method comprises the additional step, after placing the locator extraluminally proximate the first and second blood vessels, of removably stabilizing the locator relative to a bodily surface proximate at least one blood vessel, whereby the locator is substantially immobilized with respect to a blood vessel while so attached.

8. A method as set forth in claim 1, further comprising the additional step, after observing the working element to have established a path fluidly connecting the lumen of the first blood vessel to the lumen of the second blood vessel, of placing the catheter shaft in the path so established by the working element to maintain the path.

9. A method as set forth in claim 8, wherein the catheter shaft includes at least one lumen having a proximal fluid path opening and a distal fluid path opening, and the method comprises the additional step of positioning the proximal end of the lumen in the first blood vessel and the distal end of the lumen in the second blood vessel to allow blood to flow between the first and second vessel.

10. A method as set forth in claim 1, wherein the occlusion is in the lumen of the first blood vessel, the method comprising the additional step, after observing the working element to have established a path fluidly connecting the lumen of the first blood vessel to the lumen of the second blood vessel, of:
   advancing and steering the working element until the working element is observed to have extended the path so made to fluidly communicate with the lumen of the first blood vessel, whereby a path is created from the first blood vessel into the second blood vessel and continuing from the second blood vessel back into the first blood vessel, the path having a first end in the lumen of the first blood vessel proximal to the occlusion and a second end in the lumen of the first blood vessel distal to the occlusion.

11. A method as set forth in claim 1, further comprising the step of:
   establishing a path with a first end fluidly communicating with the lumen of the first blood vessel which is a vein and a second end fluidly communicating with the lumen of the second blood vessel which is an artery at a place proximal to an occlusion.

12. A method as set forth in claim 1, further providing the catheter shaft with a distal end, and further providing the working element with a nose cone disposed on the distal end of the catheter shaft.

13. A method as set forth in claim 1, further providing a plurality of slots partially circumscribing the distal end zone of the catheter shaft.

14. A method as set forth in claim 1, further providing a plurality of rings disposed in the distal end zone of the catheter shaft for defining paths for the steering wires.

15. A method as set forth in claim 1, further comprising the step of:
   establishing a fluid path created between the first and second blood vessels with a length, the catheter shaft includes a lumen having proximal end and a distal end, and the proximal end and distal end are separated by at least approximately the length of the fluid path, whereby the lumen of the catheter shaft provides a blood perfusion path while the catheter shaft is placed in the fluid path.

16. A method as set forth in claim 1, wherein the first blood vessel is an artery and the second blood vessel is a vein proximate the artery, the method further comprising the step, after advancing the working element until the working element is observed to have established a path fluidly connecting the lumen of the first blood vessel to the lumen of the second blood vessel, of placing a stent graft in the fluid path, the stent graft directing arterial blood from the fluid path into the lumen of the vein distal to the fluid path to arterialize the vein distal to the fluid path.

17. A method as set forth in claim 1, wherein the first blood vessel is an artery and the second blood vessel is a vein proximate the artery, the method further comprising the steps, after advancing the working element until the working element is observed to have established a path fluidly connecting the lumen of the first blood vessel to the lumen of the second blood vessel, of:

occluding the vein at a location proximal to the fluid path, the occlusion directing arterial blood from the fluid path into the lumen of the vein distal to the fluid path; and placing a stent in the fluid path sot that the fluid path is kept open and the vein distal to the fluid path is arterialized.

18. A method as set forth in claim 1, wherein the first blood vessel is a vein and the second blood vessel is an artery proximate the vein, the method further comprising the steps, after advancing the working element until the working element is observed to have established a path fluidly connecting the lumen of the first blood vessel to the lumen of the second blood vessel, of:

placing a stent in the fluid path, and occluding the vein at a location proximal to the fluid path, the occlusion directing arterial blood from the fluid path into the lumen of the vein distal to the fluid path so that the fluid path is kept open and the vein distal to the fluid path is arterialized.

19. An arterial catheter apparatus comprising:

an elongated flexible catheter shaft having a distal end zone and at least one longitudinal lumen extending along at least a portion of the catheter shaft and the distal end zone;

a working element disposed at the distal end zone of the catheter shaft;

a steering member comprising a plurality of steering wires slidably disposed in the catheter shaft and coupled to a retaining ring disposed in the distal end zone, wherein braid-reinforced tubes confine each of the plurality of steering wires;

a tissue-penetrating wire at least partially disposed in the lumen of the catheter shaft and extendable into the distal end zone; and a locator with an imaging device to provide guidance for the working element and tissue-penetrating wire during treatment of an occlusion.

20. A catheter apparatus as set forth in claim 19, wherein the working element is formed with a substantially conical configuration.

* * * * *